(12) United States Patent
Levy

(10) Patent No.: US 7,390,654 B2
(45) Date of Patent: Jun. 24, 2008

(54) AVOIDANCE OF UNDESIRABLE REPLICATION INTERMEDIATES IN PLASMID PROPAGATION

(75) Inventor: John Levy, Canyon Country, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 10/437,830

(22) Filed: May 13, 2003

(65) Prior Publication Data

US 2003/0180949 A1 Sep. 25, 2003

Related U.S. Application Data

(62) Division of application No. 09/715,835, filed on Nov. 16, 2000, now Pat. No. 6,709,844.

(51) Int. Cl.
*C12N 15/68* (2006.01)
*C07H 21/04* (2006.01)

(52) U.S. Cl. .................... 435/320.1; 435/69.4
(58) Field of Classification Search ............... 435/320.1
See application file for complete search history.

(56) References Cited

U.S. PATENT DOCUMENTS

| | | | | |
|---|---|---|---|---|
| 4,937,190 | A * | 6/1990 | Palmenberg et al. | ....... 435/69.1 |
| 5,168,062 | A | 12/1992 | Stinski | |
| 5,385,839 | A | 1/1995 | Stinski | |
| 5,589,466 | A | 12/1996 | Felgner et al. | |
| 5,679,647 | A | 10/1997 | Carson et al. | |
| 5,681,942 | A * | 10/1997 | Buchwald et al. | .......... 536/23.5 |
| 5,994,104 | A * | 11/1999 | Anderson et al. | ........ 435/69.52 |
| 7,026,156 | B1 * | 4/2006 | Clark et al. | .............. 435/252.3 |
| 2002/0103165 | A1 * | 8/2002 | Bot et al. | ................... 514/100 |
| 2003/0212027 | A1 * | 11/2003 | Barbera-Guillem et al. | ... 514/44 |

OTHER PUBLICATIONS

Clontech Catalog, 1995/1996, p. 182.*
Verma et al. (Nature 389:239-242 (1997).*
Palu et al. J. Biotechnol. 68:1-13 (1999).*
Fox, ASM News, 66(2):Feb. 1-3, 2000.*
Sambrook et al., Molecular Cloning, A Laboratory Manual, second ed., Cold Spring Harbor Laboratory Press, 1989, pp. 16.5-16.6.*
Invitrogen caralog website, http://www.invitrogen.com/content/sfs/manuals/pcdna3.1_man.pdf.*
Bolivar, et al., *Proc. Natl. Acad. Sci. USA*, 74(12):5265-5269, 1977, "Origin of Replication of pBR345 Plasmid DNA."
Chang, et al., *Journal of Virology*, 64(1):264-277, 1990, "The Palindromic Series I Repeats in the Simian Cytomegalovirus Major Immediate-Early Promoter Behave as Both Strong Basal Enhancers and Cyclic AMP Response Elements."
Clontech, *Catalog 2000*, pp. 125, 224-227, 223, "Innovative Tools to Accelerate Discovery."
Coskun-Ari, et al., *The Journal of Biological Chemistry*, 272(42):26448-26456, 1997, "Sequence-specific Interactions in the Tus-*Ter* Comlex and the Effect of Base Pair Substitutions on Arrest of DNA Replication in *Escherichia coli*."
Duke, et al., *Journal of Virology*, 66(3):1602-1609, 1992, "Sequence and Structural Elements That Contribute to Efficient Encephalomyocarditis Virus RNA Translation."
Hill, et al., *Proc. Natl. Acad. Sci. USA*, 87:241-2485, 1990, "*Escherichia coli* Tus Protein Acts to Arrest the Progression of DNA Replication Forks in vitro."
Invitrogen, *1999 Product Catalog*, pp. 101, 153.
Khatri, et al., *Cell*, 59:667-674, 1989, "The Replication Terminator Protein of *E. coli* is a DNA Sequence-Specific Contra-Helicase."
Krasilnikov, et al., *Nucleic Acids Research*, 25(7):1339-1346, 1997, "Mechanisms of Triplex-caused Polymerization Arrest."
Mobley, et al., *Journal of Virology*, 72(8):6592-6601, 1998, "Role of the Transcription Start Site Core Region and Transcription Factor YY1 in Rous Sarcoma Virus Long Terminal Repeat Promoter Activity."
Peter, et al., *Cell*, 94:819-827, 1998, "The Structure of Supercoiled Intermediates in DNA Replication."
Promega, *Life Science Catalog 1999*, pp. 1.1, 11.4, 13.4-13.5.
Samadashwily, et al., *Nature Genetics*, 17:298-304, 1997, "Trinucleotide Repeats Affect DNA Replication in vivo."
Santamaria, et al., *The Journal of Biological Chemistry*, 273(50):33386-33396,1998, "DnaB Helicase is Unable to Dissociate RNA-DNA Hybrids."
Stratagene, *Catalog 1999, Tools and Technology for Life Sciences*, pp. 17-18, 21, 54.
Viguera, et al., *The Journal of Biological Chemistry*, 271(37):22414-22421, 1996, "The ColE1 Unidirectional Orgin Acts as a Polar Replication Fork Pausing Site."
Viguera, et al., *Nucleic Acids Research*, 28(2):498-503, 2000, "Visualisation of Plasmid Replication Intermediates Containing Reversed Forks."
pTargeT™ Mammalian Expression System Technical Manual, Technical Manual No. 044, pp. 1-30 (Promega Corp. 2001).
NCBI Sequencer Viewer, Cloning vector pEGFP-C1, complete sequence, enhanced green fluorescent protein (egfp) and neomycin phosphotransferase genes, complete cds . . . [gi:1377914], Accession U55763.
NCBI Sequence Viewer, Cloning vector pEGFP-C2 with enhanced green fluorescent protein gene, complete sequence . . . [gi:1373315], Accession U57606.
NCBI Sequence Viewer, Cloning vector pEGFP-C3 with enhanced green fluorescent protein gene, complete sequence . . . [gi:1373318], Accession U57607.
NCBI Sequence Viewer, Cloning vector pEGFP-N1 complete sequence, enhanced green fluorescent protein (egfp) and neomycin phosphotransferase genes, complete cds . . . [gi:1377911], Accession U55762.

(Continued)

*Primary Examiner*—Nancy Vogel
(74) *Attorney, Agent, or Firm*—Sonnenschein Nath & Rosenthal LLP

(57) ABSTRACT

Disclosed herein are improved plasmid shuttle vectors, vaccines based on them, and methods related to their construction and use. Particular arrangements of functional elements of such plasmids, namely origins of replication and eukaryotic transcription/translation control elements, which give rise to generally undesirable side-products upon propagation of the plasmids in bacterial culture are disclosed. These side-products apparently arise as terminated replication intermediates. Strategies both to eliminate accumulation of these side-products, and to make them useful as a vaccine adjuvant, are described.

12 Claims, 14 Drawing Sheets

OTHER PUBLICATIONS

NCBI Sequence Viewer, Cloning vector pEGFP-N2 with enhanced green fluorescent protein gene, complete sequence . . . [gi:1543069], Accession U57608.

NCBI Sequence Viewer, Cloning vector pEGFP-N3 with enhanced green fluorescent protein gene, complete sequence . . . [gi:1543070], Accession U57609.

pVAX1, Invitrogen Catalog No. V260-20, Version B, 062102, 25-0256, pp. i-11 (Invitrogen 1998-2002).

"Living Colors™ Enhanced GFP Vectors—The brightest GFP chromophore variant for maximal sensitivity in mammalian cells," *CLONTECHniques*, Apr. 1996.

"Living Colors™ EYFP Vectors—New options for expressing enhanced yellow fluorescent protein (EYFP) in mammalian cells," *CLONTECHniques*, Jan. 1998.

"Living Colors™ pEBFP-N1 & -C1 Vectors, condon-optimized fusion vectors for enhanced blue fluorescent protein," *CLONTECHniques*, Jul. 1997.

"Living Colors™ Enhanced GFP Vectors—The brightest chromophore variant for maximal sensitivity in mammalian cells," *CLONTECHniques*, Apr. 1996.

"New Living Colors™ Vectors—The evolution of a revolution continues," *CLONTECHniques*, Jul. 1998.

"Living Colors™ Destabilized EGFP Vectors—Rapid-turnover green fluorescent protein—the cutting edge of GFP technology," *CLONTECHniques*, Apr. 1998.

"Living Colors™ Destabilized ECFP & EYFP Vectors—Monitor changes in gene expression in cyan or yellow," *CLONTECHniques*, Jul. 1999.

US 6,008,200, 12/1999, Krieg (withdrawn)

* cited by examiner

A: Lambda BsteII
B: pCTL007 in DH10B
C: pCTL007 in DH5α

A: pCTL007
B: CLONE 1
C: CLONE 10

```
                  AAACG CCAGC AACGC GGCCT TTTTA CGGTT CCTG
GGCGGA GCCTA TGGAA AAACG CCAGC AACGC GGCCT TTTTA CGGTT CCTG 2250
             ***** ***** ***** ***** ***** ***** ****

GCCTTT TGCTG GCCTT TTGCT CACAT GTTCT TGCTG CTTCG CGATG TACG
GCCTTT TGCTG GCCTT TTGCT CACAT GTTCT TGCTG CTTCG CGATG TACG 2300
****** ***** ***** ***** ***** ***** ***** ***** ***** ****

GGCCAG ATATA CGCGT TGACA TTGAT TATTG ACTAG TTATT AATAG TAAT
GGCCAG ATATA CGCGT TGACA TTGAT TATTG ACTAG TTATT AATAG TAAT 2350
****** ***** ***** ***** ***** ***** ***** ***** ***** ****

CAATTA CGGGG TCATT AGTTC ATAGC CCATA TATGG AGTTC CGCGT TACA
CAATTA CGGGG TCATT AGTTC ATAGC CCATA TATGG AGTTC CGCGT TACA 2400
****** ***** ***** ***** ***** ***** ***** ***** ***** ****

TAACTT ACGGT AAATG GCCCG CCTGG CTGAC CGCCC AACGA CCCCC GCCC
TAACTT ACGGT AAATG GCCCG CCTGG CTGAC CGCCC AACGA CCCCC GCCC 2450
****** ***** ***** ***** ***** ***** ***** ***** ***** ****

ATTGAC GTCAA TAATG ACGTA TGTTC CCATA GTAAC GCCAA TAGGG ACTT
ATTGAC GTCAA TAATG ACGTA TGTTC CCATA GTAAC GCCAA TAGGG ACTT 2500
****** ***** ***** ***** ***** ***** ***** ***** ***** ****

TCCATT GACGT CAATG GGTGG AGTAT TTACG GTAAA CTGCC CACTT GGCA
TCCATT GACGT CAATG GGTGG AGTAT TTACG GTAAA CTGCC CACTT GGCA 2550
****** ***** ***** ***** ***** ***** ***** ***** ***** ****

GTACAT CAAGT GTATC ATATG CCAAG TACGC CCCCT ATTGA CGTCA ATGA
GTACAT CAAGT GTATC ATATG CCAAG TACGC CCCCT ATTGA CGTCA ATGA 2600
****** ***** ***** ***** ***** ***** ***** ***** ***** ****

CGGTAA ATGGC CCGCC TGGCA TTATG CCCAG TACAT GACCT TATGG GACT
CGGTAA ATGGC CCGCC TGGCA TTATG CCCAG TACAT GACCT TATGG GACT 2650
****** ***** ***** ***** ***** ***** ***** ***** ***** ****

TTCCTA CTTGG CAGTA CATCT ACGTA TTAGT CATCG CTATT ACCAT GGTG
TTCCTA CTTGG CAGTA CATCT ACGTA TTAGT CATCG CTATT ACCAT GGTG 2700
****** ***** ***** ***** ***** ***** ***** ***** ***** ****

ATGCGG TTTTG GCAGT ACATC AATGG GCGTG GATAG CGGTT TGACT CACG
ATGCGG TTTTG GCAGT ACATC AATGG GCGTG GATAG CGGTT TGACT CACG 2750
****** ***** ***** ***** ***** ***** ***** ***** ***** ****

GGGATT TCCAA GTCTC CA
GGGATT TCCAA GTCTC CACCC CATTG ACGTC AATGG GAGTT TGTTT TGGC 2800
****** ***** ***** **
```

Upper sequence: ~600 bp RI
Lower sequence: alignment to pCTL007

FIG. 2D

```
        10         20         30         40         50
AAACGCCAGC AACGCGGCCT TTTTACGGTT CCTGGGCTTT TGCTGGCCTT 60         70         80         90        100
TTGCTCACAT GTTCTTGACT CTTCGCGATG TACGGGCCAG ATATACGCGT 110        120        130        140        150
TGACATTGAT TATTGACTAG TTATTAATAG TAATCAATTA CGGGGTCATT 160        170        180        190        200
AGTTCATAGC CCATATATGG AGTTCCGCGT TACATAACTT ACGGTAAATG 210        220        230        240        250
GCCCGCCTGG GTGACCGCCC AACGACCCCC GCCCATTGAC GTCAATAATG 260        270        280        290        300
ACGTATGTTC CCATAGTAAC GCCAATAGGG ACTTTCCATT GACGTCAATG 310        320        330        340        350
GGTGGACTAT TTACGGTAAA CTGCCCACTT GGCAGTACAT CAAGTGTATC 360        370        380        390        400
ATATGCCAAG TACGCCCCCT ATTGACGTCA ATGACGGTAA ATGGCCCGCC 410        420        430        440        450
TGGCATTATG CCCAGTACAT GACCTTATGG GACTTTCCTA CTTGGCAGTA 460        470        480        490        500
CATCTACGTA TTAGTCATCG CTATTACCAT GGTGATGCGG TTTTGGCAGT 510        520        530        540        550
ACATCAATGG GCGTGGATAG CGGTTTGACT CACGGGGATT TCCAAGTCTC 560        570        580        590        600
CACCCCATTG ACGTCAATGG GAGTTTGTTT TGGCACCAAA ATCAACGGGA 610        620        630        640
CTTTCCAAAA TGTCGTAACA ACTCCGCCCC ATTGACGCAA ATGGG
```

KEY
- 19 base pair repeat
- 18 base pair repeat
- 16 base pair repeat
- 21 base pair repeat
- NDE restriction enzyme site

FIG. 2E

CMV promoter and enhancer deletion at *Ase* I site

A: pCTL007
B: pL33A
C: pVAX-1
D: pCTL007ΔCMV

A: pCTL007
B: pcDNA3.1

SEQUENCE LISTING

<160> NUMBER OF SEQ ID NOS: 3

<210> SEQ ID NO 1
<211> LENGTH: 552
<212> TYPE: DNA
<213> ORGANISM: Artificial Sequence
<220> FEATURE:
<223> OTHER INFORMATION: Replication intermediate from plasmid pCTL007

<400> SEQUENCE: 1

```
aaacgccagc aacgcggcct ttttacggtt cctggccttt tgctggcctt ttgctcacat      60
gttcttgctg cttcgcgatg tacgggccag atatacgcgt tgacattgat tattgactag     120
ttattaatag taatcaatta cggggtcatt agttcatagc ccatatatgg agttccgcgt     180
tacataactt acggtaaatg gcccgcctgg ctgaccgccc aacgaccccc gcccattgac     240
gtcaataatg acgtatgttc ccatagtaac gccaatagggactttccatt gacgtcaatg     300 ggtggagtat ttacggtaaa ctgcccactt ggcagtacat caagtgtatc atatgccaag     360 tacgcccccct attgacgtca atgacggtaa atggcccgcc tggcattatg cccagtacat     420
gaccttatgg gactttccta cttggcagta catctacgta ttagtcatcg ctattaccat     480
ggtgatgcgg ttttggcagt acatcaatgg gcgtggatag cggtttgact cacggggatt     540
tccaagtctc ca                                                         552
```

<210> SEQ ID NO 2
<211> LENGTH: 588
<212> TYPE: DNA
<213> ORGANISM: Artificial Sequence
<220> FEATURE:
<223> OTHER INFORMATION: plasmid pCTL007

<400> SEQUENCE: 2

```
gcggagccta tggaaaaacg ccagcaacgc ggccttttta cggttcctgc cttttgctgg      60
ccttttgctc acatgttctt gctgcttcgc gatgtacggc cagatatacg cgttgacatt     120
gattattgac tagttattaa tagtaataat tacggggtca ttagttcata gcccatatat     180
ggagttccgc gttacaaact tacggtaaat ggcccgcctg gctgaccgcc caacgacccc     240
```

-continued

```
cgcccttgac gtcaataatg acgtatgttc ccatagtaac gccaataggg acttccattg     300
acgtcaatgg gtggagtatt tacggtaaac tgcccacttg gcatacatca agtgtatcat     360
atgccaagta cgcccctat tgacgtcaat gaggtaaatg gcccgcctgg cattatgccc      420
agtacatgac cttatgggac ttcctacttg gcagtacatc tacgtattag tcatcgctat     480
taccatggtg tgcggttttg gcagtacatc aatgggcgtg gatagcggtt tgactcacgg     540
gatttccaag tctccacccc attgacgtca atgggagttt gttttggc                  588

<210> SEQ ID NO 3
<211> LENGTH: 645
<212> TYPE: DNA
<213> ORGANISM: CYTOMEGALOVIRUS

<400> SEQUENCE: 3
aaacgccagc aacgcggcct ttttacggtt cctgggcttt tgctggcctt ttgctcacat       60
gttcttgact cttcgcgatg tacgggccag atatacgcgt tgacattgat tattgactag     120
ttattaatag taatcaatta cggggtcatt agttcatagc ccatatatgg agttccgcgt     180
tacataactt acggtaaatg gcccgcctgg ctgaccgccc aacgacccc gcccattgac       240 gtcaataatg acgtatgttc ccatagtaac gccaataggg actttccatt gacgtcaatg     300
ggtggactat ttacggtaaa ctgcccactt ggcagtacat caagtgtatc atatgccaag     360
tacgccccct attgacgtca atgacggtaa atggcccgcc tggcattatg cccagtacat     420
gaccttatgg gactttccta cttggcagta catctacgta ttagtcatcg ctattaccat     480
ggtgatgcgg ttttggcagt acatcaatgg gcgtggatag cggtttgact cacggggatt     540
tccaagtctc cacccattg acgtcaatgg gagtttgttt tggcaccaaa atcaacggga      600
ctttccaaaa tgtcgtaaca actccgcccc attgacgcaa atggg                     645
```

AVOIDANCE OF UNDESIRABLE REPLICATION INTERMEDIATES IN PLASMID PROPAGATION

CROSS REFERENCE TO RELATED APPLICATIONS

The present application is a divisional of and claims priority to U.S. application Ser. No. 09/715,835, filed on Nov. 16, 2000 now U.S Pat. No. 6,709,844. The disclosure of the prior application is hereby expressly incorporated by reference in its entirety.

BACKGROUND OF THE INVENTION

1. Field of the Invention

The invention disclosed herein relates to methods and compositions for the efficient production of bacterial plasmid-based shuttle vectors free of linear plasmid-derived DNA contaminants, and particularly such vectors as might be used in DNA vaccination and gene therapy.

2. Description of the Related Art

The application of recombinant DNA technology to eukaryotic cells has come to rely on shuttle vectors, plasmids that can be readily produced in bacterial culture but include elements that function in eukaryotic cells. Generally such plasmids contain a bacterial origin of replication and a selectable marker. In most cases the origin of replication is a high copy number origin so that many copies of the plasmid can replicate simultaneously in each bacterial cell thereby providing higher yields in production. The most commonly used origins of replications include pMB1, ColE1, and pUC. These origins are closely related and can be found in high and low copy number variants. The selectable marker serves to ensure that only bacteria containing the plasmid survive in culture. The eukaryotic elements most often consist of a viral or eukaryotic promoter linked to a protein coding frame leading to production of a peptide or protein when the plasmid is transduced into an appropriate eukaryotic host cell. In other cases transcription from the promoter accomplishes expression of a viral genomic RNA, leading to production of virus particles, or an antisense RNA. Various other elements may be included depending on the functions sought and these functions may dictate the arrangement of the elements involved. However no rules have been described for the arrangement of functionally unrelated elements.

SUMMARY OF THE INVENTION

The present invention is directed to methods and compositions for avoiding the production of certain side-products to plasmid replication. When the plasmid is used in pharmaceutical products, as in gene therapy or DNA vaccination procedures, these side-products complicate production and the acquisition of regulatory approval. The diversion of replicative machinery and chemical precursors constitutes a drain on bacterial metabolism potentially reducing yield of the desired product. Moreover, the side products require characterization and very possibly removal by an additional purification step.

The side-products appear to be replication intermediates on which synthesis is terminated at particular sequences found in eukaryotic transcription and translation control elements. These side products are produced generally when the bacterial origin of replication is 5' of, and parallel in orientation to, the eukaryotic element(s).

In one aspect of the invention the production of the side-products is eliminated by inverting the orientation of the origin of replication relative to the eukaryotic element(s). In another aspect of the invention production of the side-products is eliminated by increasing the distance between the origin of replication and the eukaryotic element(s). In yet another aspect of the invention an immunostimulatory sequence is inserted between the origin of replication and the eukaryotic element(s) so that the side products may be used as a vaccine adjuvant.

BRIEF DESCRIPTION OF THE DRAWINGS

Note: For ease of presentation graphic representations of plasmids have been presented as if these molecules were linear, when if fact they are circular.

FIG. 2D: Sequence of ~600 bp replication intermediate (SEQ ID NO: 1), upper sequence, compared to plasmid (SEQ ID NO: 2), lower sequence.

FIG. 2E: Locations of repeat elements in CMV enhancer (SEQ ID NO: 3).

DETAILED DESCRIPTION OF THE PREFERRED EMBODIMENT

In propagating and purifying plasmid shuttle vectors for use as DNA vaccines short double-stranded linear pieces of DNA are observed in some cases. These fragments range in size from approximate 200 to 700 base pairs (bp). A combination of restriction mapping and sequencing shows that the sequence of these short double-stranded pieces of DNA is contained in the plasmid. Further, the sequence is consistent with terminated replication intermediates, that is they share a common end coincident with the site of initiation of DNA replication.

Figure 1A:
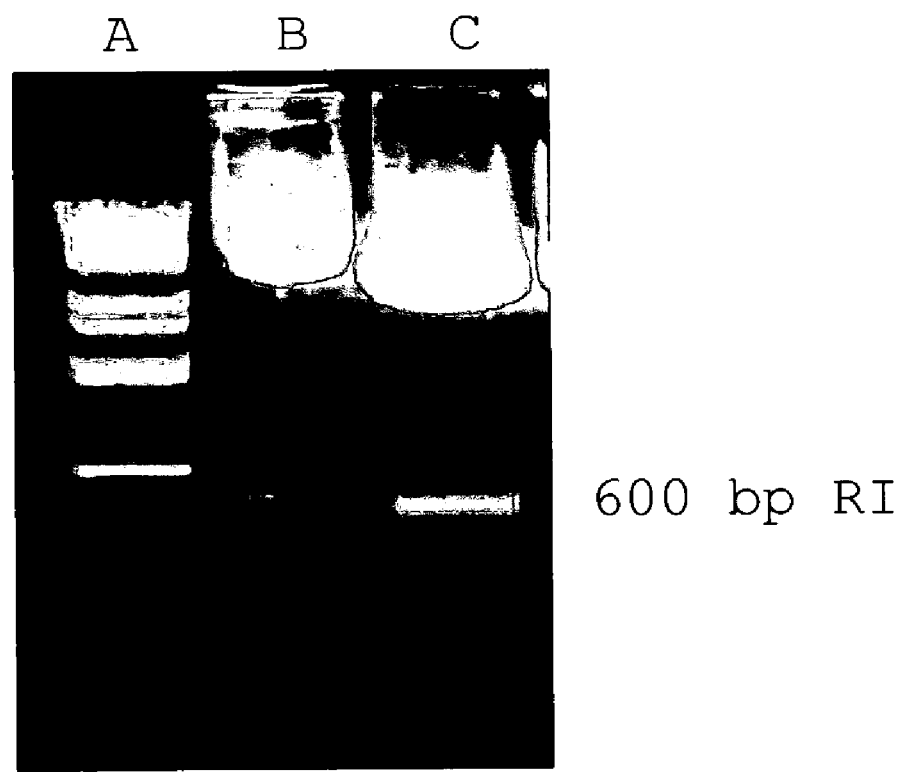
FIG. 1A: Replication intermediates produced in two bacterial strains.

This phenomenon was initially observed in a plasmid derived from pVAX1, a product of Invitrogen Corp. (Carlsbad, Calif.), which has been constructed to comport with FDA recommendations for plasmids to be used as DNA vaccines. (The use of polypeptide-encoding DNA as a vaccine is described in U.S. Pat. No. 5,589,466, entitled "INDUCTION OF A PROTECTIVE IMMUNE RESPONSE IN A MAM- MAL BY INJECTING A DNA SEQUENCE" and U.S. Pat. No. 5,679,647, entitled "METHODS AND DEVICES FOR IMMUNIZING A HOST AGAINST TUMOR-ASSOCIATED ANTIGENS THROUGH ADMINISTRATIONS OF NAKED POLYNUCLEOTIDES WHICH ENCODE TUMOR-ASSOCIATED ANTIGENIC PEPTIDES" and in U.S. patent application Ser. No. 09/380,534 entitled A METHOD OF INDUCING A CTL RESPONSE, which are herein incorporated by reference in their entirety). While both the culture conditions and the bacterial host strain used in propagating the plasmid influenced the amount of linear DNA produced, production of these pieces of DNA did not appear to be an accident of the particular parameters being used (FIG. 1).

A linear piece of DNA of approximately 600 bp was gel purified and subjected to restriction analysis which showed that it shared sequence with the plasmid immediately 3' of the origin of replication. The DNA was treated with mung bean nuclease and cloned into a sequencing vector and the sequence obtained matched that expected for a fragment beginning at the initiation site for DNA synthesis, thereby supporting its identification as a terminated replication intermediate.

The arrangement of functional elements in pVAX1 is somewhat a typical, though not unique, in that the bacterial origin of replication is situated so that there is minimal sequence interposed between it and a eukaryotic enhancer/promoter element, and so that the replication fork proceeds through the enhancer/promoter element in the 5'-3' direction, i.e., they are parallel. The enhancer/promoter found in pVAX1 is derived from the cytomegalovirus immediate-early promoter (hereinafter the CMV promoter). The enhancer region of the CMV promoter contains various repeated sequence elements, which are described in greater detail in U.S. Pat. Nos. 5,168,062 and 5,385,839 both entitled "TRANSFER VECTORS AND MICROORGANISMS CONTAINING HUMAN CYTOMEGALOVIRUS IMMEDIATE-EARLY PROMOTER-REGULATORY DNA SEQUENCE", as well as Chang et al., *J. Virol* 64:264-77, 1990, which are incorporated herein by reference in their entirety. Repeat elements are a common feature of eukaryotic enhancer/promoters and serve a functional role, generally related to transcription factor binding. The replication intermediates produced during propagation of pVAX1 derived plasmids all terminate in the vicinity of these repeat elements. In particular termination is noted near the 18- and 19-base pair repeats, the former of which is adjacent to the 16-base pair repeat defined in simian CMV (Chang et al. supra). That these elements are involved in causing termination of replication is further supported by the observation that deletion of particular elements eliminates accumulation of particular replication intermediates (see FIG. 2).

Figure 3:
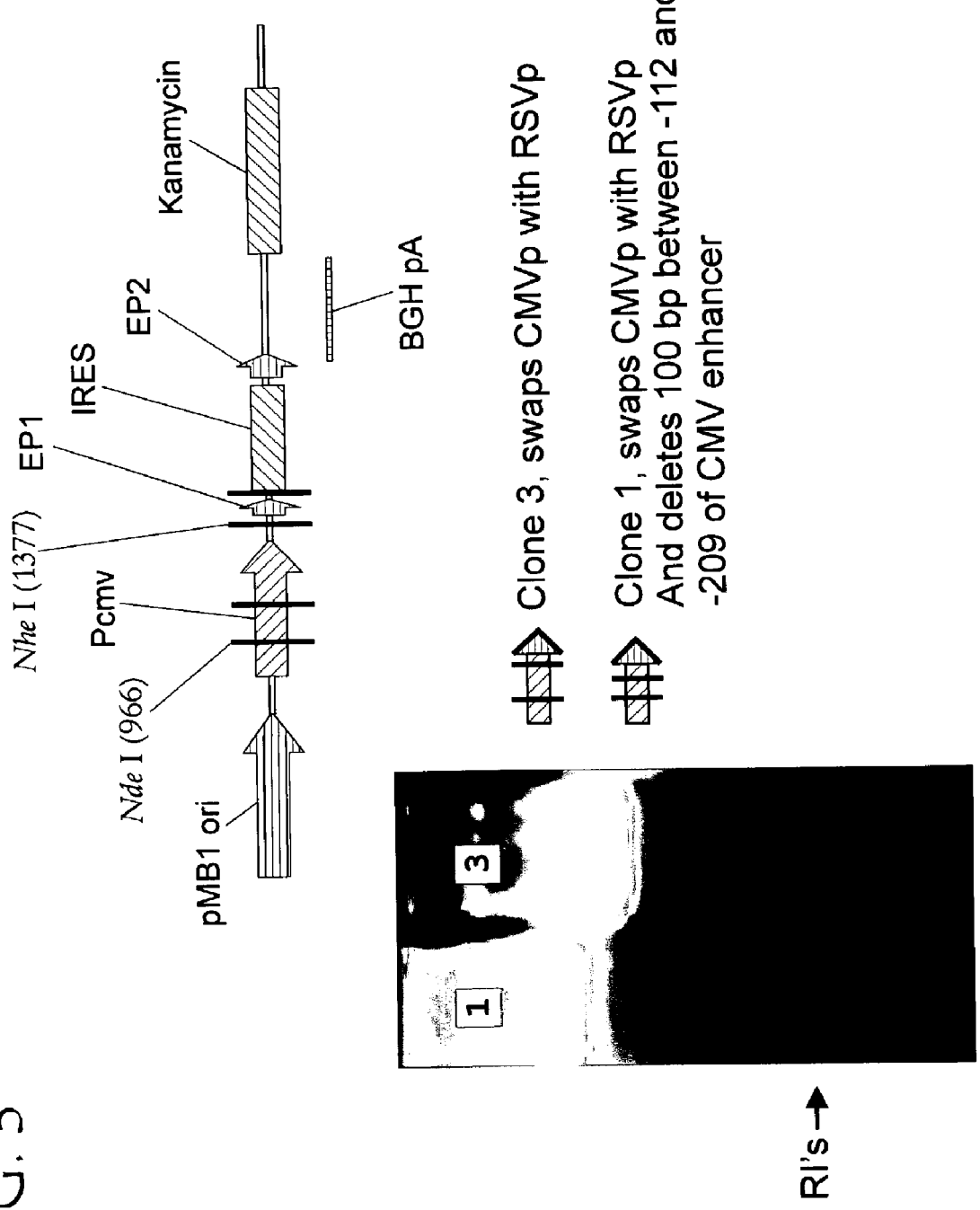
FIG. 3: Graphical representation of promoter swaps and agarose gel image of corresponding replication intermediates.

Replacement of the CMV promoter region (retaining the enhancer) with the promoter from the Rous sarcoma virus (RSV) long terminal repeat (LTR) also resulted in the accumulation of replication intermediates (See FIG. 3). The replication intermediates observed upon propagation of the RSV promoter containing plasmid appear to terminate in a region containing a binding motifs for the YY1 transcription factor (Mobley, C.M. & Sealy, L., J. Virol. 72: 6592-6601, 1998). Due to the functional role of repeat elements and other transcription factor binding sites and the apparent involvement of such sequences in the termination of replication, it can be difficult to find or modify a promoter so that it does not contribute to this phenomenon but retains useful functionality.

One of the pVAX1 derivatives also contains an encephalomyocarditis (EMC) virus internal ribosome entry site (IRES) 3' of the CMV promoter. The IRES is a sequence which adopts a complex secondary structure that facilitates ribosome assembly and translation initiation thereby allowing the genomic RNAs of picornaviruses to also serve as messenger RNA (mRNA). (The IRES is more fully described in U.S. Pat. No. 4,937,190 entitled "TRANSLATION ENHANCER", and in Duke G. M., et al. J. Virol. 66:1602-1609, 1992, which are incorporated herein by reference in their entirety). Replication intermediates accumulate to significantly higher levels upon propagation of this derivative than for pVAX1 itself. This effect is prevented by deletion of the picornaviral sequence leading up to and including the beginning of the D-loop domain at the 5' end of the IRES. However, even when the CMV promoter is deleted, a replication intermediate that terminates within the IRES, is formed. (See FIG. 4).

Figure 5:
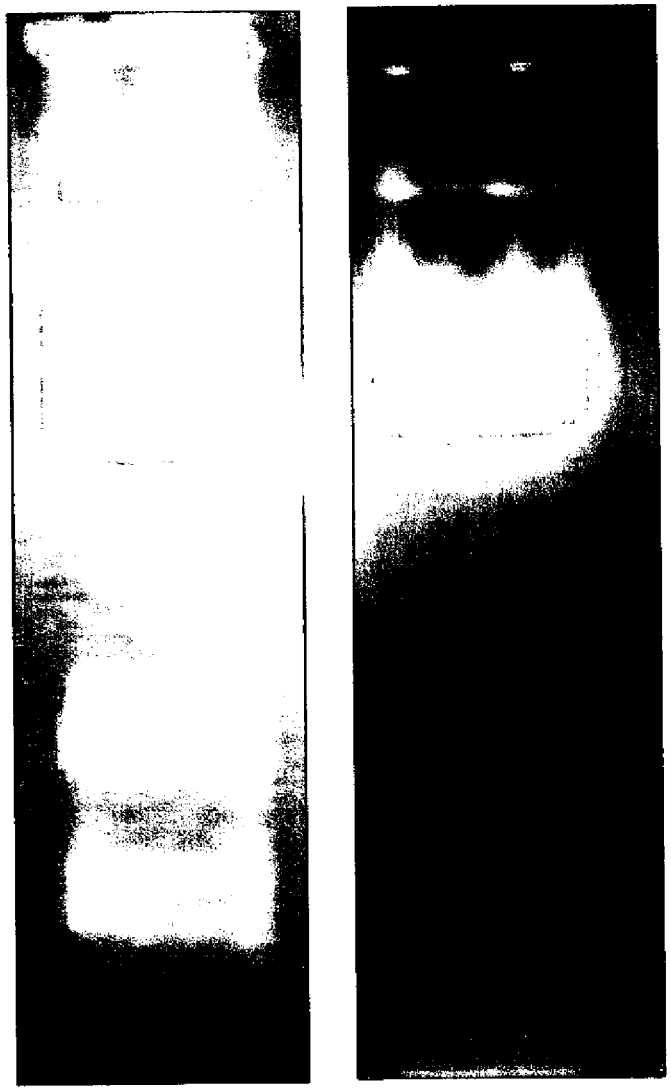
FIG. 5: Agarose gel image showing absence of replication intermediates from pcDNA3.1.

It is not immediately obvious why these elements should cause termination of DNA replication. Moreover these elements coexist in a variety of other plasmids without giving rise to the accumulation of replication intermediates (See FIG. 5). However, we have worked with another plasmid, pL33A, derived from a different backbone but with an arrangement of these elements analogous to pVAX1, that also produces similar replication intermediates. Consideration of the structure of pVAX1 and pL33A on one hand, versus the structure of the replication intermediate-free plasmids on the other, help to suggest some possible mechanisms. The repeat elements may fortuitously bind some bacterial DNA binding protein or may participate in some secondary structure, either of which might interfere with progression of the replication fork. The apparent interference could arise simply from proximity to the sites of assembly of the replication complex and initiation of replication, or by some directionally-defined interaction perhaps by interfering particularly with lagging or leading strand synthesis. Additionally, the relatively high level of activity at the origin of replication apparently contributes to the phenomenon as pIRES, (a product of Clontech Laboratories Inc., Palo Alto, Calif.), again with a similar arrangement of elements, but utilizing a low copy number version of the ColE1 origin of replication, does not accumulate replication intermediates upon propagation (see FIG. 5).

The simplest approach to obviating any of these mechanisms, while maintaining the function of the plasmid, is to invert the orientation of the origin of replication relative to the eukaryotic elements so that they are anti-parallel. This will cause the replication fork to proceed through the eukaryotic elements in the 3'-5' direction disrupting any directionality-dependent interference. Moreover, since the plasmid is asymmetric with regard to the positioning of the origin of replication and the eukaryotic elements, inverting the orientation will also increase the distance between these interfering elements. Such a construct does in fact eliminate accumulation of replication intermediates (see FIG. 6). The distance between the interfering elements can also be increased separately without inverting the orientation of the origin of replication relative to the eukaryotic elements. In preferred embodiments, in plasmids characterized by production of replication intermediates, a distance of less than about 1000 bp (1 kb) produces such replication intermediates, while a distance greater than about 1.5 kb typically does not. In other embodiments, the shorter distance, which favors intermediates, can be from about 500 bp to about 700 bp, or about 900 bp to about 1200 bp, while the longer distance, which disfavors intermediates, can be from about 1300 to about 1600 bp, or from about 1800 to about 2000, about 2200, or about 2500 bp.

A variety of commercially available vectors have an arrangement of origin of replication and eukaryotic control elements similar to that described above and thus may benefit from the modifications herein disclosed. These include, without limitation: pEBFP-N1, pECFP-N1, pEGFP-N1, pEGFP-N2, pEGFP-N3, pEYFP-N1, pEBEP-C1, pECFP-C1, pEGFP-C1, pEGFP-C2, pEGFP-C3, pEYFP-C1, pEGFP-F, pCMS-EGFP, pIIRES2-EGFP, pd2ECFP-N1, pd2EGFP-N1, pd2EYFP-N1, pd1EGFP-N1 and sold by Clontech Laboratories Inc. (Palo Alto, Calif.); pCMV-Script, pCMV-Tag, pDual, pBK-CMV and pBK-RSV sold by Stratagene (La Jolla, Calif.); and pTARGET®, pCI, and pCI-Neo sold by Promega Corporation (Madison, Wis.).

Accumulation of replication intermediates will generally be viewed as undesirable, as a drain on bacterial metabolism and as a contaminant requiring additional characterization and purification steps. However, as it may not be absolutely necessary to exclude them from a pharmaceutical product, one may optionally imbue the replication intermediates with a desirable activity. In an embodiment of this invention one or more immunostimulatory sequences (ISS) are inserted between the origin of replication and the eukaryotic control element(s) so that the replication intermediates will contain ISS. Thus when the plasmid is used as a DNA vaccine the replication intermediates will serve as an adjuvant, increasing the overall potency of the vaccine. Examples of ISS are disclosed in U.S. Pat. No. 6,008,200 "IMMUNOMODULATORY OLIGONUCLEOTIDES" which is herein incorporated by reference in its entirety.

EXAMPLES

Example 1

Figure 1B:
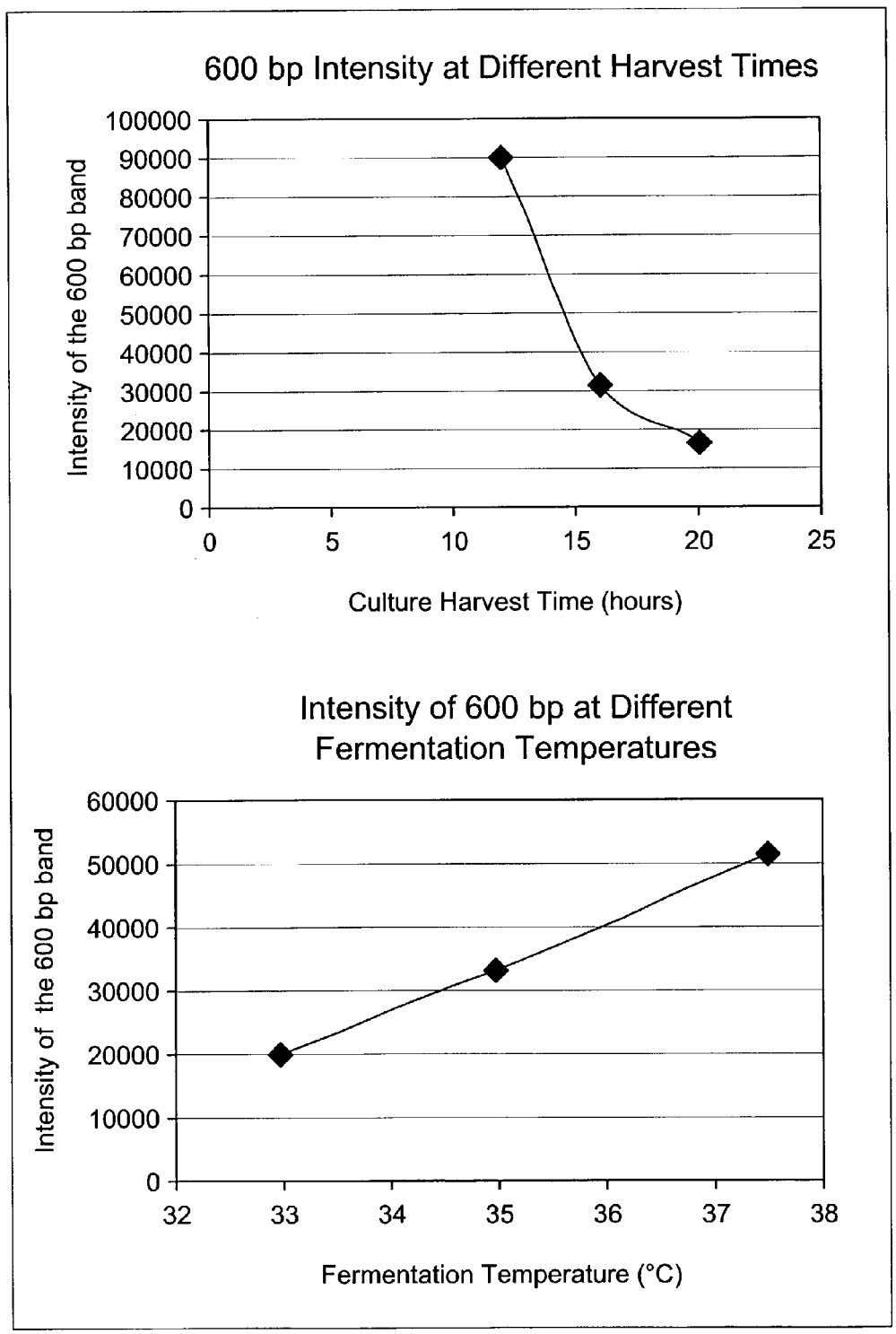
FIG. 1B: Effect of length of culture and temperature on accumulation of replication intermediate.

The plasmid pCTL002, a pVAX1 derivative, was propagated using in two different bacterial host strains, DH5α (sold by Life Technologies, Rockville, Md.) and DH10B (also known as Top10 as sold by Invitrogen Corporation, Carlsbad, Calif.) in 1.5 liter cultures using LB+kanamycin at 37° C. for 16 hrs. at 250 rpm in a rotary shaking incubator. Approximately two-thirds less replication intermediate accumulated in DH10B compared to DH5α (see FIG. 1A). Using the above conditions and DH10B the effect of temperature was examined by comparing cultures grown at 33, 35, and 37° C. and it was found that the ratio of plasmid to replication intermediate could be improved approximately 2.5-fold (see FIG. 1B). Twelve, sixteen, and twenty hour cultures were also compared, indicating that longer cultures resulted in less accumulation of replication intermediate relative to plasmid (FIG. 1B). In other experiments no effect of speed of shaking was noted.

Example 2

Figure 2A:
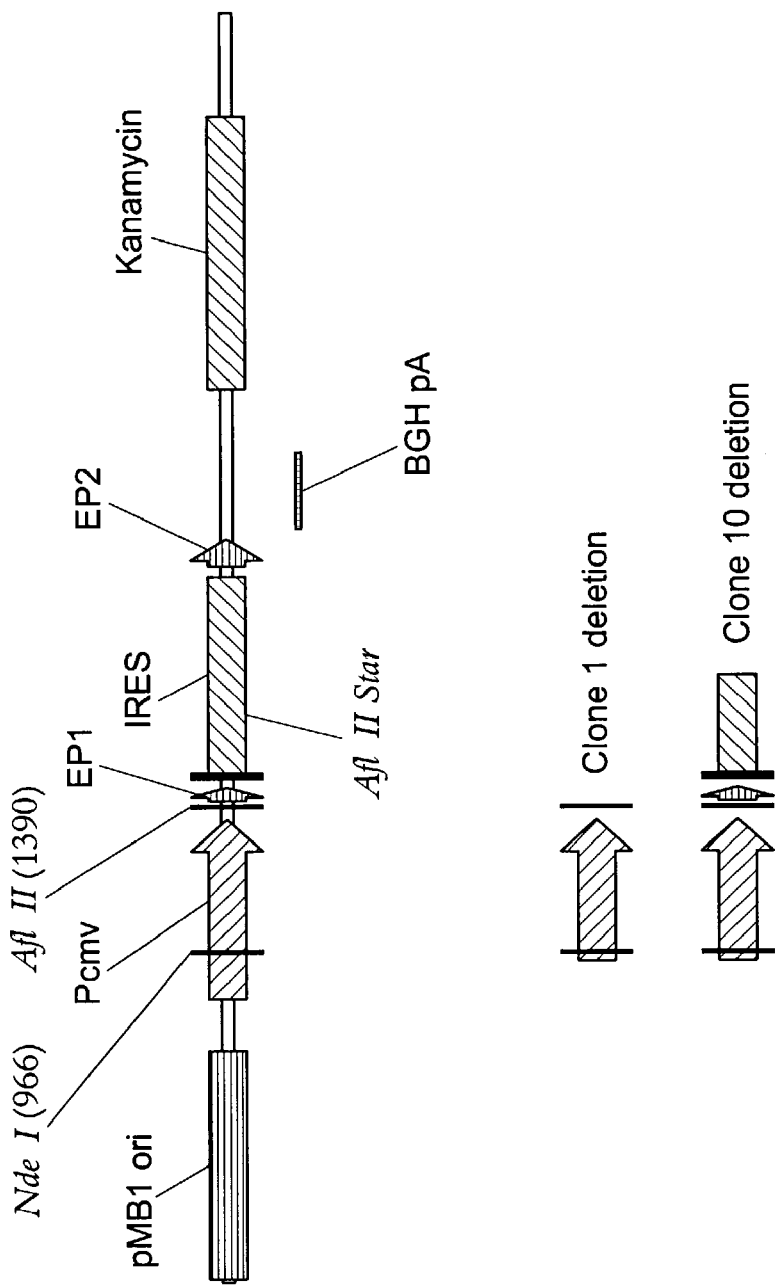
FIG. 2A: Graphical representation of deletions in pCTL007 (partial CMV enhancer/promoter and IRES).
Figure 2B:
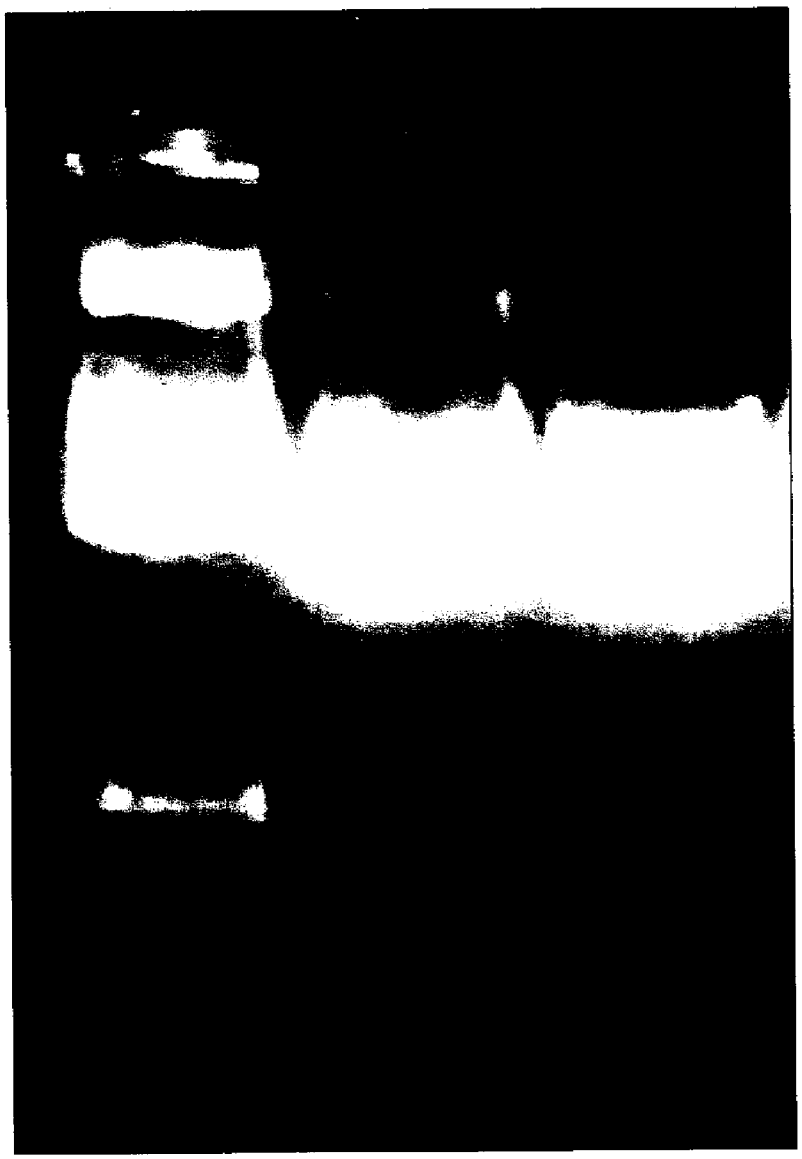
FIG. 2B: Agarose gel image of corresponding replication intermediates.
Figure 2C:
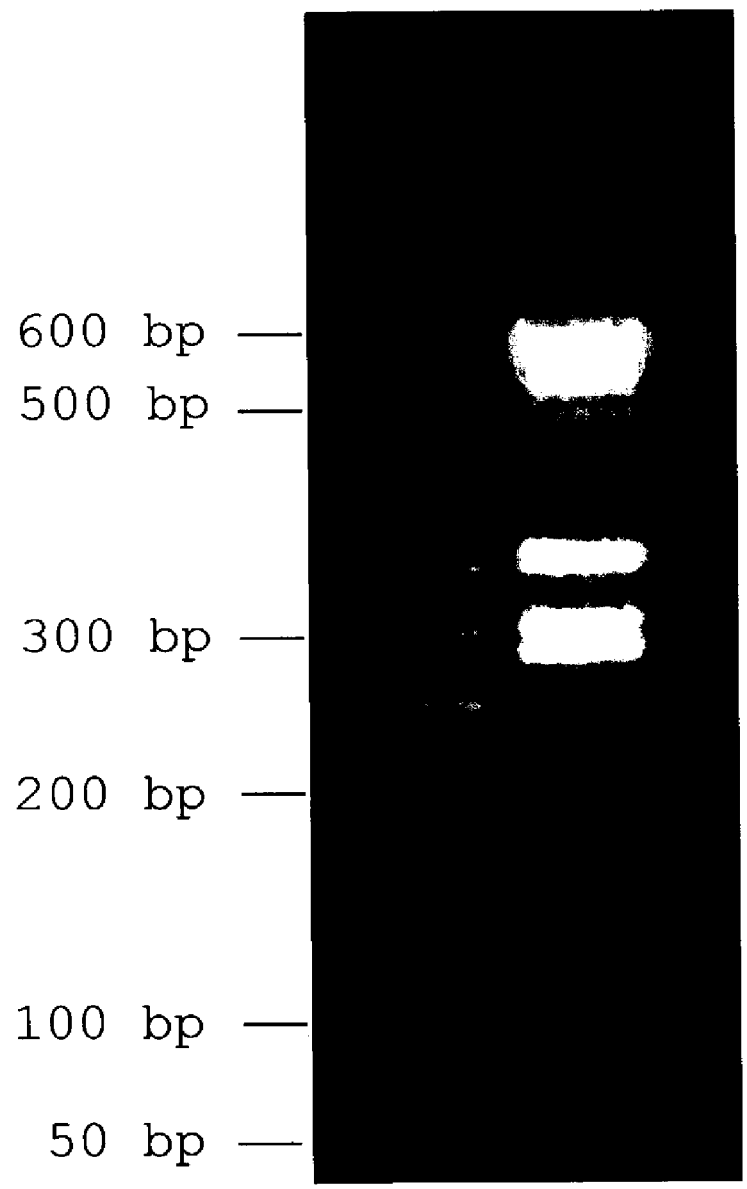
FIG. 2C: High resolution agarose gel image of replication intermediates.

Two deletions were prepared in pCTL007 beginning at the NdeI site located midway through the CMV enhancer and continuing to either 1) the AflII site 5' of start codon; or 2) an AflII* site ~100 bases into the IRES (see FIG. 2A). Deletion 1) eliminated the ~600 bp intermediate as well as an ~360 bp intermediate (see FIG. 2B, clone 1), A ~300 bp intermediate was unaffected. Deletion 2) eliminated all of the replication intermediates (see FIG. 2B, clone 10).

More concentrated material and gels providing greater resolution reveal a total of five replication intermediates in pCTL007 preparations (see FIG. 2C): The ~300 bp band above is actually a doublet of 280 and 310 bp bands. Additionally there is a faint band at 490 bp. The ~600 bp band can also be seen to be closer to 575 bp. All of these sizes are based on relative mobility of the bands versus commercial size standards in agarose gel electrophoresis and assessed by eye, and are thus still approximate. The cloning process removed an unknown number of bases in single stranded overhangs from the 580 bp fragment, but the literature creates an expectation of 15-20 bases (Bolivar, F., et al., Proc. Nati. Acad Sci. USA 74:5265-5269, 1977). Sequence of the cloned fragment showed it to be 552 bp, (see figure 2D) consistent with the size seen on agarose gels given the accuracy of that method. Based on these data the replication intermediates would terminate in the vicinity of the following CMV enhancer repeats: the 575 bp fragment at the 19-base pair repeat at −146 to −128 of the CMV sequence (CCCCATTGACGTCAATGGG; SEQ ID NO: 4, which corresponds to bp 553 to 571 of SEQ ID NO :3); the 500 bp fragment at the 16-base pair repeat at −207 to −192 (TTTGGCAGTACATCAA; SEQ ID NO: 5, which corresponds to bp 492 to 507 of SEQ ID NO: 3) of the CMV sequence; the 360 bp fragment at the 19-base pair repeat at −334 to −315 (CCCCTATTGACGTCAATGA; SEQ ID NO: 6, which corresponds to bp 366 to 384 of SEQ ID NO: 3) of the CMV sequence; the 310 and 280 bp fragments at the 18- and 16-base pair repeats at −427 to −410 (CCAATAGGGACTTTCCAT: SEQ ID NO: 7, which corresponds to bp 272 to 289 of SEQ ID NO: 3) and −413 to −398 of the CMV sequence (CCATTGACGTCAATGG; SEQ ID NO: 8, which corresponds to bp 286 to 301 of SEQ ID NO: 3), respectively (see FIG. 2E).

Example 3

The 411 bp NdeI-NheI fragment of pCTL007, corresponding to most of the CMV promoter, but excluding the 18- and 16-base pair repeats at −427 to −410 and −413 to −398 of the CMV sequence, was replaced with an RSV promoter plus variable amounts of the removed CMV sequences. One construct, effectively deleting −209 onward of the CMV sequence and thus the termination site giving rise to the 580 bp fragment, nonetheless still gives rise to a fragment of similar size (see FIG. 3, clone 3). The termination site for this fragment is within the RSV promoter sequences, in the general vicinity of the transcriptional start site. Binding sites for several transcription factors are present although similarity to the transcription factor binding sites represented by the CMV repeat sequences is not readily discerned.

Example 4

Figure 4A:
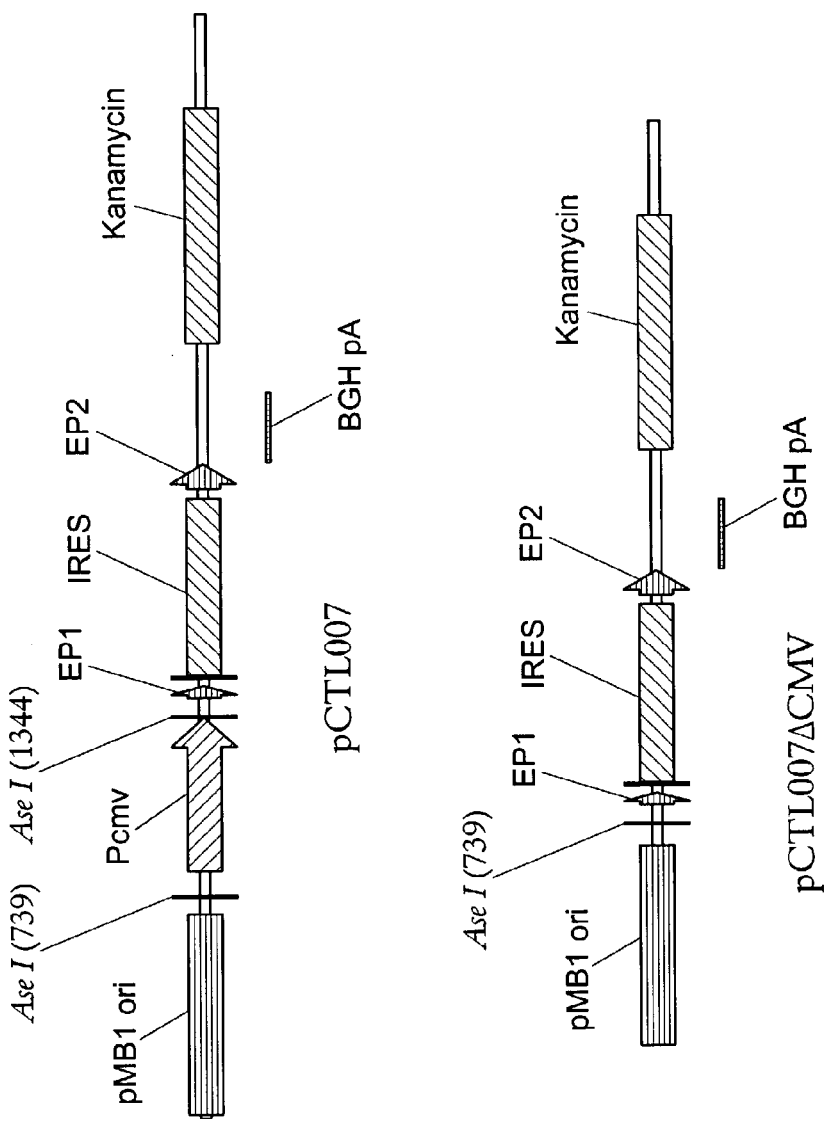
FIG. 4A: Graphical representation of deletions in pCTL007 (CMV enhancer/promoter).
Figure 4B:
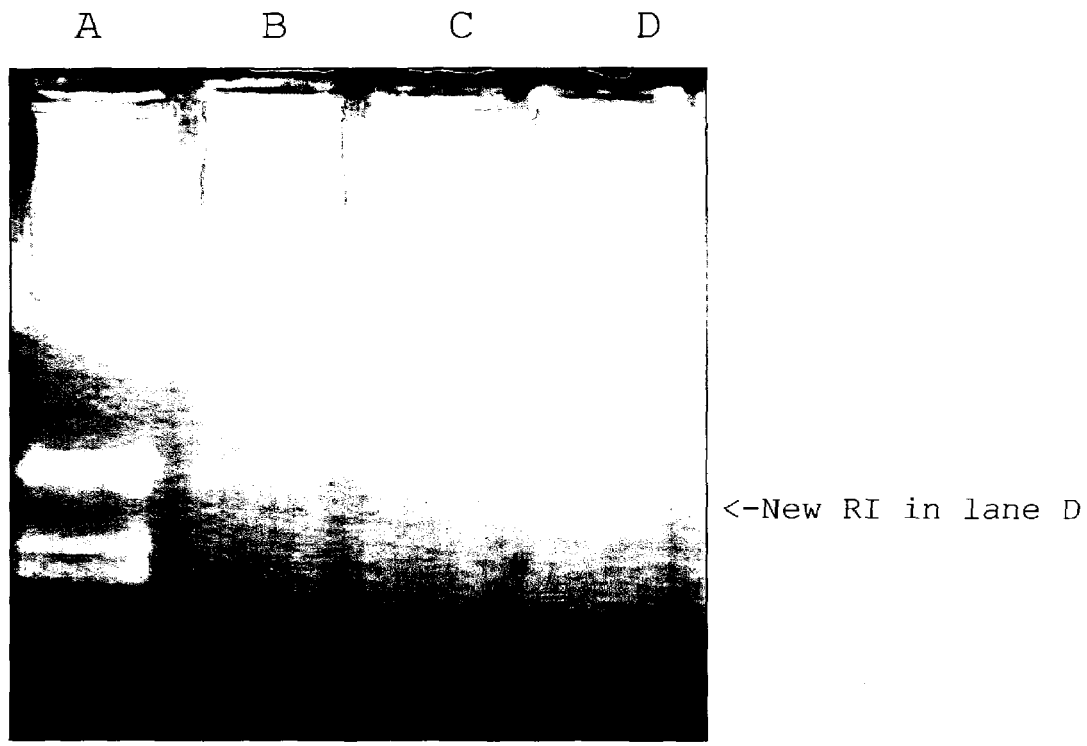
FIG. 4B: Agarose gel image of replication intermediates from various plasmids.
Figure 4C:
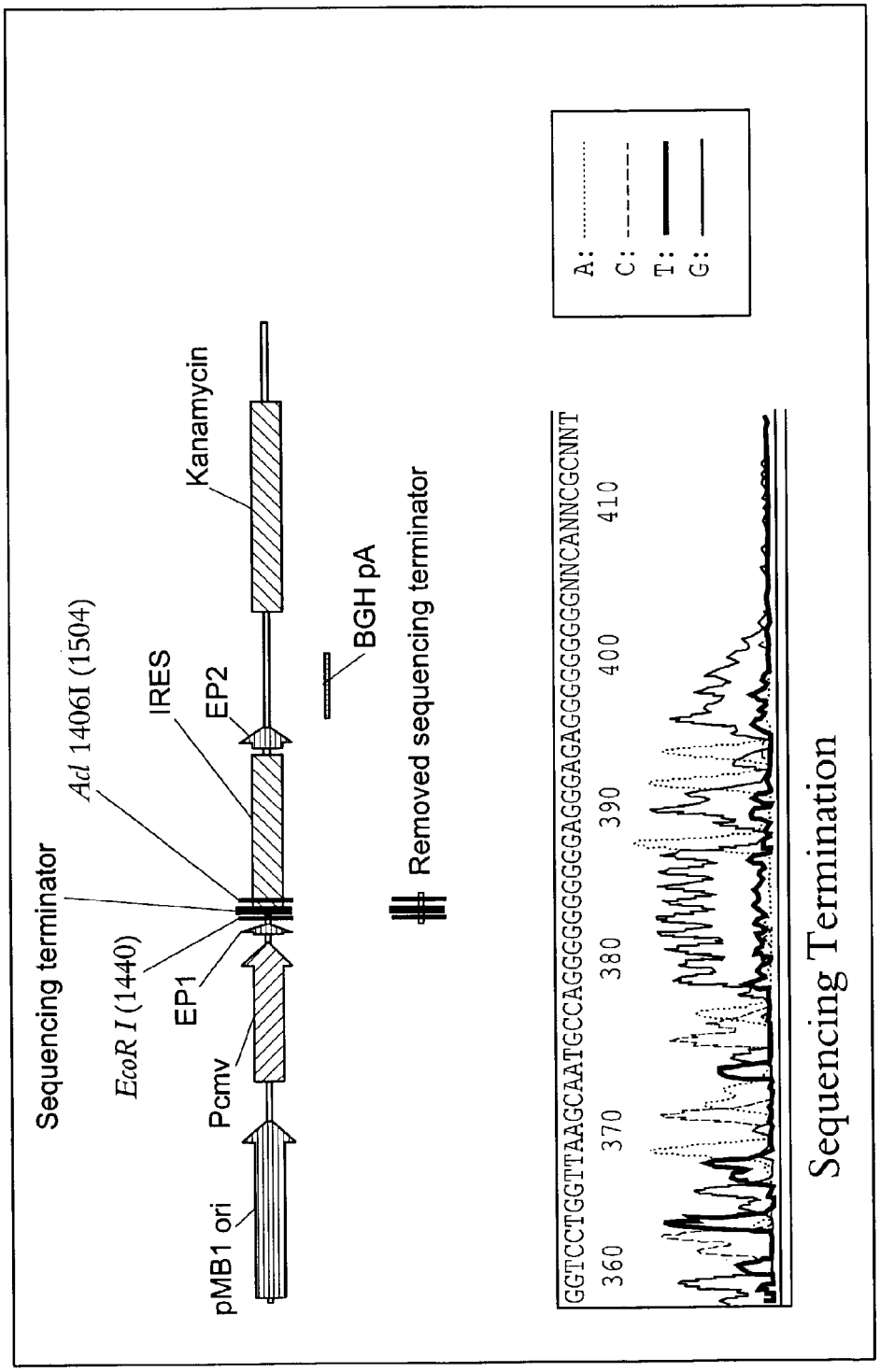
FIG. 4C: Graphical representation indicating deleted EMC sequence leading up to and including the beginning of the D-loop of the IRES; and sequencing terminator.

A 605 bp AseI fragment containing the entire CMV enhancer/promoter was removed and the remainder ligated (see FIG. 4A). When this plasmid was propagated one replication intermediate of roughly 470 bp was observed so that the termination site falls within the IRES, most likely within the I-loop (see FIG. 4B).

The IRES also greatly increases the amount of termination occurring at the CMV promoter sites when both elements are present. This effect can be reversed by deleting the EMC sequence leading up to and including the beginning of the D-loop of the IRES (up to base 522 of the EMC sequence). This sequence also tends to terminate sequencing reactions (see FIG. 4C).

Example 5

The plasmids pcDNA3.1 (Invitrogen Corp., Carlsbad, Calif.) and pIRES (Clontech Laboratories Inc., Palo Alto, Calif.) both contain the CMV enhancer and similar origins of replication to pVAX1. However neither gives rise to the accumulation of replication intermediates (see FIG. 5). In pcDNA3.1 the origin of replication and CMV promoter are in an anti-parallel orientation. A low copy number version of the ColE1 origin of replication is used in pIRES. In contrast pL33A, based on yet another backbone, but using a high copy number origin of replication in an orientation parallel to the CMV promoter gives rise to a family of replication intermediates very similar to those seen with pVAX1-derived plasmids (see FIGS. 4B & 6B).

Example 6

Figure 6A:
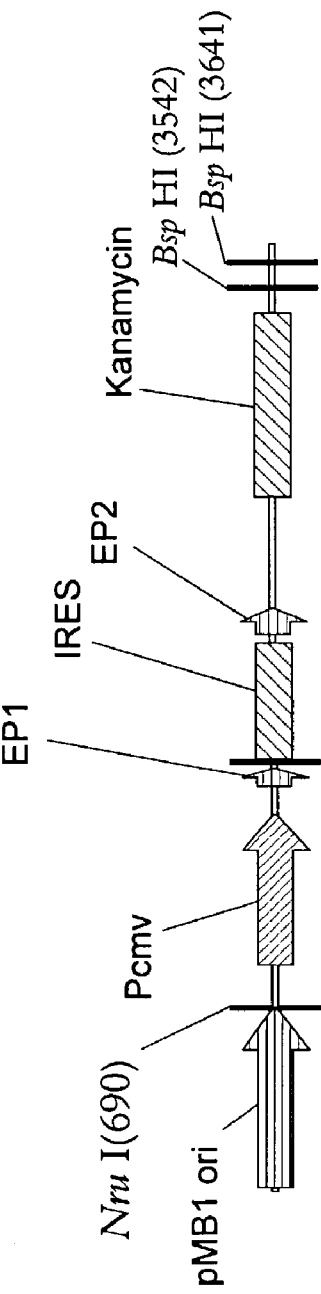
FIG. 6A: Graphical representation of construction of plasmid with origin of replication in inverted orientation.
Figure 6A:
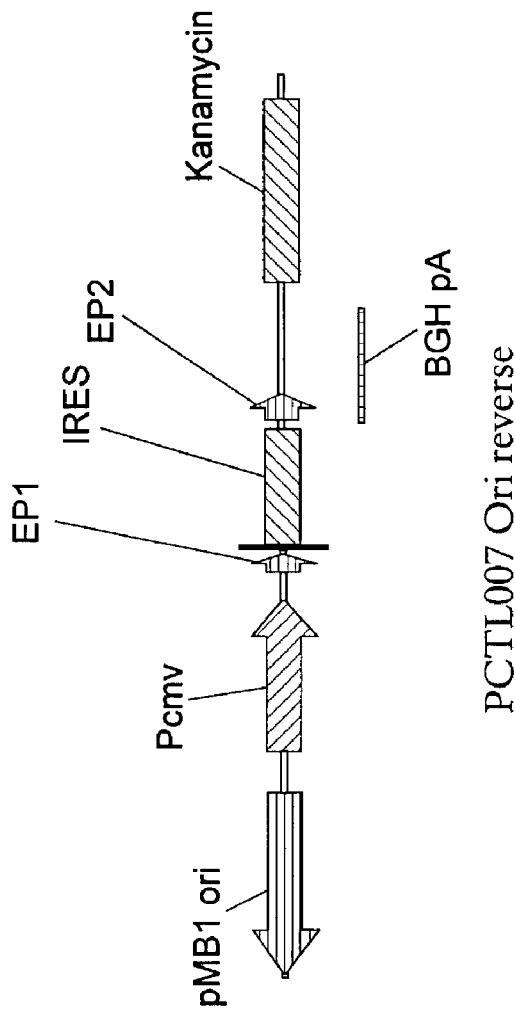
Figure 6B:
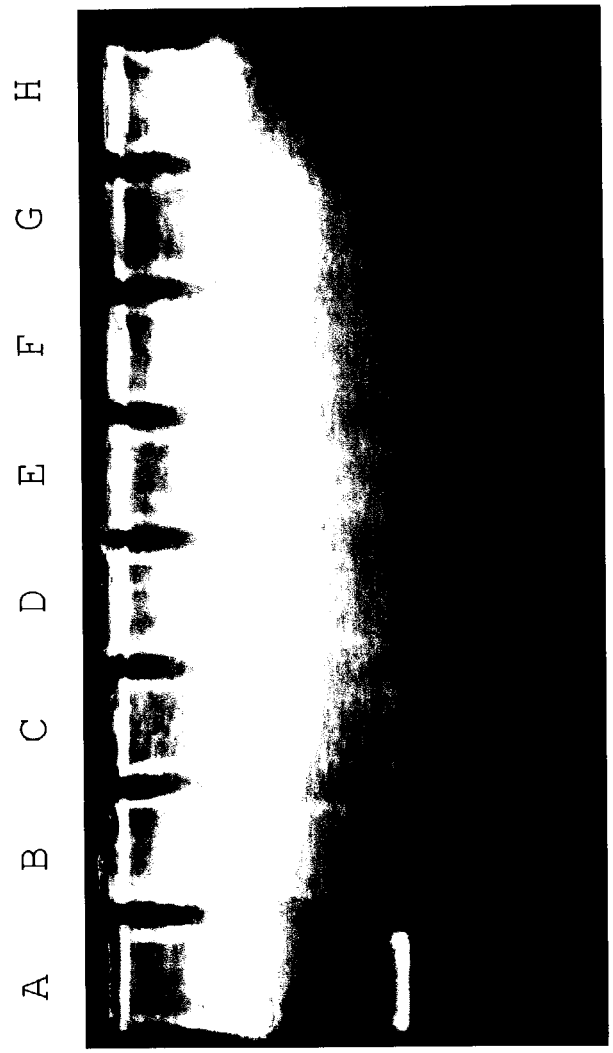
FIG. 6B: Agarose gel image showing absence of replication intermediates from plasmids with inverted origin of replication.

The plasmid pCTL007 was digested with BspHI and NruI, the staggered ends filled in with Klenow, and the fragments ligated together (see FIG. 6A). The resultant clones were screened by PCR to identify clones in which the origin of replication had been inverted. Upon propagation no accumulation of replication intermediates were observed with plasmids containing the inverted origin of replication (see FIG. 6A). It was possible that a long replication intermediate was being formed by synthesis in the opposite direction and co-migrating with supercoiled plasmid. To rule out this possibility an AseI digest was performed. This digest would have liberated fragments of a few hundred base pairs from any replication intermediate proceeding around the plasmid in the opposite direction and terminating in the CMV promoter, however, no such fragments were observed (see FIG. 6B).

Example 7

The plasmid pCTL007 is digested with NruI. A double stranded oligonucleotide containing an ISS sequence of 5'-TCAACGTT-3' is ligated to the plasmid recircularizing it. The plasmid is propagated and co-purified with the resulting ISS-containing replication intermediates and administered to an animal as a vaccine.

What is claimed is:

1. In a plasmid selected from the group consisting of a pVAX1 vector, a pEBFP-N1 vector, a pECFP-N1 vector, a pEGFP-N1 vector, a pEGFP-N2 vector, a pEGFP-N3 vector, a pEYFP-N1 vector, a pEBFP-C1 vector, a pECFP-C1 vector, a pEGFP-C1 vector, a pEGFP-C2 vector, a pEGFP-C3 vector, a pEYFP-C1 vector, a pEGFP-F vector, a pCMS-EGFP vector, a pIRES2-EGFP vector, a pd2ECFP-N1 vector, a pd2EGFP-N1 vector, a pd2EYFP-N1 vector, a pd1 EGFP-N1 vector, a pCMV-Script vector, a pCMV-Tag vector, a pDual vector, a pBK-CMV vector, a pBK-RSV vector, a pTARGET vector, a pCI vector, and a pCI-Neo vector, said plasmid having a high copy number prokaryotic origin of replication and at least one eukaryotic control element located at a first distance in a direction of replication, wherein the first distance is less than about 1200 bp from the origin of replication, and wherein the plasmid produces a first population of liner replication side products, the improvement comprising: an increased distance in a direction of replication between the origin of replication and the control element, wherein the increased distance is at least about 1.5 kb, and wherein the improved plasmid produces a second population of linear replication side products, wherein the second population is substantially smaller than the first population.

2. The improved plasnild of claim 1 which is a modified form of a pVAX1 vector.

3. The improved plasmid of claim 1, wherein the origin of replication and the control element are in a parallel orientation.

4. The improved plasmid of claim 1, wherein the origin of replication and the control element are in an antiparallel orientation.

5. The improved plasrnid of claim 1, wherein said first distance is less tan about 1 kb.

6. The improved plasmid of claim 1, wherein the prokaryotic origin of replication is pUC, pMB1 or ColE1.

7. The improved plasmid of claim 1, wherein the control element is selected from the group consisting of an enhancer, a promoter, and an IRES.

8. The improved plasmid of claim 7, wherein the control element comprises a CMV promoter and/or enhancer.

9. The improved plasmid of claim 7, wherein the control element comprises an RSV LTR promoter.

10. The improved plasmid of claim 7, wherein the control element comprises a picornaviral IRES.

11. The improved plasmid of claim 10, wherein the IRES is an EMC virus IRES.

12. The improved plasmid of claim 7, wherein the control element comprises a CMV enhancer 16 base pair repeat, 18 base pair repeat, or 19 base pair repeat.

* * * * *